(12) United States Patent
List et al.

(10) Patent No.: US 9,028,426 B2
(45) Date of Patent: May 12, 2015

(54) DEVICE AND METHOD FOR WITHDRAWING BODY FLUID

(75) Inventors: Hans List, Hesseneck-Kailbach (DE);
Wolfgang Rödel, Heidelberg (DE);
Christian Hörauf, Oftersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 727 days.

(21) Appl. No.: 12/854,665

(22) Filed: Aug. 11, 2010

(65) Prior Publication Data

US 2011/0054274 A1    Mar. 3, 2011

Related U.S. Application Data

(63) Continuation of application No. PCT/EP2009/051581, filed on Feb. 11, 2009.

(30) Foreign Application Priority Data

Feb. 11, 2008  (EP) .................................. 08151294

(51) Int. Cl.
*A61B 5/15*     (2006.01)
*A61B 5/151*    (2006.01)

(52) U.S. Cl.
CPC ........... *A61B 5/1411* (2013.01); *A61B 5/15115* (2013.01); *A61B 5/15103* (2013.01); *A61B 5/15123* (2013.01); *A61B 5/15117* (2013.01)

(58) Field of Classification Search
CPC ............... A61B 5/1405; A61B 5/1411; A61B 5/14514; A61B 5/14532; A61B 5/150022; A61B 5/15117; A61B 5/15123; A61B 5/1513; A61B 5/15107; A61B 5/15109; A61B 5/15111; A61B 5/15113; A61B 2010/008
USPC ........................... 600/583, 584; 606/181, 182
See application file for complete search history.

(56) References Cited

U.S. PATENT DOCUMENTS

| | | | |
|---|---|---|---|
| 6,375,626 B1 | 4/2002 | Allen et al. | |
| 7,025,774 B2 | 4/2006 | Freeman et al. | |
| 2002/0177788 A1 | 11/2002 | Hodges et al. | |
| 2003/0199911 A1* | 10/2003 | Boecker et al. | 606/181 |

(Continued)

FOREIGN PATENT DOCUMENTS

| | | |
|---|---|---|
| EP | 1 709 906 | 10/2006 |
| EP | 1 725 169 | 11/2006 |

(Continued)

*Primary Examiner* — Adam Eiseman
(74) *Attorney, Agent, or Firm* — Bose McKinney & Evans LLP

(57) ABSTRACT

The invention relates to a device for removing body fluid with a puncture element that can puncture the skin of a body part. The device includes a housing structure for body fluids obtained from the skin puncture and a puncture drive for a back and forth movement of the puncture element. The duration of withdrawal movement is longer than the duration of the forward movement. The puncture drive is designed to withdraw the puncture element in a first withdrawal phase of the withdrawal movement with a maximum withdrawal speed of more than 0.02 m/s. A second retraction phase follows the first retraction phase. Body fluid is collected during the second retraction phase, which has a duration of between 0.3 and 0.8 seconds and/or a retraction speed of between 0.6 and 2 mm/s.

48 Claims, 1 Drawing Sheet

(56) References Cited

U.S. PATENT DOCUMENTS

| | | |
|---|---|---|
| 2003/0233112 A1 | 12/2003 | Alden et al. |
| 2004/0087990 A1 | 5/2004 | Boecker et al. |
| 2006/0195047 A1* | 8/2006 | Freeman et al. .............. 600/583 |
| 2007/0064516 A1 | 3/2007 | Briggs et al. |
| 2007/0191736 A1 | 8/2007 | Alden |
| 2007/0213682 A1 | 9/2007 | Haar et al. |
| 2008/0108910 A1* | 5/2008 | Hein et al. ................... 600/583 |
| 2008/0262388 A1 | 10/2008 | List et al. |
| 2009/0012428 A1 | 1/2009 | Kramer et al. |
| 2009/0192409 A1* | 7/2009 | Wong et al. .................. 600/583 |

FOREIGN PATENT DOCUMENTS

| | | |
|---|---|---|
| EP | 1 797 822 | 6/2007 |
| JP | 2007-527289 A | 9/2007 |
| JP | 2008-534192 A | 8/2008 |
| JP | 2009-519064 A | 4/2009 |
| JP | 2009-518062 A | 5/2009 |
| WO | WO 2005/084546 | 9/2005 |
| WO | WO 2006/105968 A1 | 10/2006 |
| WO | WO 2006105968 A1 * | 10/2006 |

* cited by examiner

DEVICE AND METHOD FOR WITHDRAWING BODY FLUID

RELATED APPLICATIONS

This application is a continuation of PCT/EP2009/051581, filed Feb. 11, 2009, which claims priority to EP08151294.9, filed Feb. 11, 2008, both of which are hereby incorporated by reference in their entirety.

BACKGROUND

The invention concerns a device for withdrawing body fluid with a lancing element that can puncture the skin of a body part and which has a receiving structure for receiving body fluid obtained from the puncture and a lancing drive for a forward and retracting movement of the lancing element, wherein the duration of the retracting movement is longer (preferably many times longer) than the duration of the forward movement. The invention additionally concerns a corresponding method for withdrawing body fluid.

For blood sugar tests it has already been proposed that automatic withdrawal of sample from the skin by puncture with a lancing element can be accomplished by carrying out the retraction movement considerably more slowly than the forward movement so that an adequate amount of sample for the test can be reliably collected. In so doing, the position of the transition from rapid to slower movement should be at only such a depth in the tissue that a receiving structure incorporated into the lancing element still makes a reliable contact with the escaping liquid. A lancing system is described in WO 2007/073870 which allows the transition position to be kept constant despite a variable lancing depth but requires considerable technical complexity.

SUMMARY

The present invention addresses the problems with the systems and methods proposed in the prior art and provides a device for reliable sample collection with limited constructional complexity, and in doing so, also reduces the painfulness of the lancing procedure.

These teachings are based on the idea of starting collection at an intermediate position under the skin which can be reached at a very high speed and which is situated at a fixed retraction distance behind the selected deepest puncture position. In this connection, the lancing element is moved in a first retraction phase of the retracting movement at a maximum retraction speed of more than 0.02 m/s. This measure allows the maximum lancing depth to be selected according to the individual skin properties in such a manner that sufficient blood capillaries are opened by the puncture while this particularly pain-intensive phase is reduced to a minimum by the rapid first return movement. The collection process then only takes place in the subsequent second retraction phase, which is designed so that body fluid flows into the receiving structure. For this purpose the duration of the skin puncture should be long enough to enable uptake of the required amount of sample. However, it has surprisingly turned out that an excessively slow movement of the lancing element impedes blood uptake. Furthermore, the collecting phase should be completed within a defined time interval in order to also suffice the boundary conditions for the lancing depth. Accordingly, it is proposed that the lancing drive retracts the lancing element from the skin during a second retraction phase for collecting body fluid into the receiving structure. The second retraction phase follows the first retraction phase in such a manner that the retraction speed is between 0.6 and 2 mm/s and/or the collecting period is in a range between 0.3 and 0.8 s.

According to an exemplary embodiment, the lancing element is pulled back during the first retraction phase by a defined first partial distance preferably of up to 0.5 mm from the deepest puncture position into an intermediate position situated under the skin surface. In this connection, the skin surface can be determined by the device by means of an appropriate reference position, for example, by a positioning for the body part or a skin detector or a predetermined lancing depth. Furthermore, the constant first retraction distance enables one to dispense with a technically complicated movement control, thus enabling a harmonious motion sequence in the region where the direction of the needle is reversed without using stop structures at the reversal point that cause unwanted vibrations.

The return movement of the lancing element preferably takes place in such a manner that the receiving structure can at least be substantially filled with body fluid during the collecting period while the lancing element still projects into the skin. In this connection it should be noted that an appreciable uptake of body fluid released into the puncture wound does not take place until after the first rapid retraction phase.

It is particularly advantageous when the duration of the forward movement and of the first retraction phase is between 0.3 to 3 ms, preferably 0.3 to 0.7 ms, thus enabling a harmonious motion sequence for the initial puncture process.

The collection period for taking up body fluid into the receiving structure should advantageously be between 0.4 and 0.5 s. In this connection, it is also particularly advantageous when the mean retraction speed of the lancing element during the second retraction phase is in a range of about 1 to 1.5 mm/s.

For a user-related collecting profile it should be possible to adjust the maximum lancing depth between about 1 and 2.5 mm.

The speed time course during the return movement of the lancing element is advantageously adapted in accordance with a variable lancing depth in such a manner that the lancing element remains inserted into the skin for a predetermined dwell period. This enables an individual adaptation of the puncture depth without constantly changing the cycle durations.

For a simpler movement control it can be advantageous when the speed time course during the retraction movement of the lancing element is preset independently of the lancing depth.

Another improvement with regard to sample collection is achieved by the fact that the speed of the lancing element in the second retraction phase is essentially constant.

A test element to which body fluid can be applied from the receiving structure is provided for a simplified handling in an integrated system. In order to substantially exclude disadvantageous changes in the samples, the total duration from the start of the retraction movement of the lancing element until loading the test element with the body fluid should be less than 5 s, preferably less than 1 to 2 s.

Another supplementary or alternative aspect of these teachings is that a test element designed to detect an analyte in the body fluid is arranged in such a manner that the transfer time for transferring the body fluid from the receiving structure onto the test element is less than 1.5 s, preferably less than 1 s and preferably less than 0.5 s. It has surprisingly turned out that adherence to this time window is particularly important for the test quality. The test element can be directly arranged on the lancing element and optionally be fluidly connected to the receiving structure via a flow path. It is also possible to arrange the test element separately and in particular physically separate from the receiving structure and to transfer the liquid by a suitable actuation, for example, with structure deformation. Reference is made in this connection to WO 2005/084530 and WO 2007/025713 as examples.

The lancing element advantageously has a sharp lancing member which penetrates in a low-pain manner into the skin during skin puncture and in particular a single needle tip.

In order to take into consideration possible dents in the skin during puncture, it is possible to register the position of the skin surface by a skin detector and/or to define it for the body part by means of a positioning unit.

Sample collection is considerably simplified by means of the fact that a channel structure and in particular a groove-shaped or slot-shaped channel structure that can be brought into contact with the body fluid at least at a distal end section during skin puncture, is incorporated into the lancing element.

Another advantageous aspect is the fact that the drive mechanism controls the forward movement and retraction movement during a first retraction phase of the lancing element whereas the drive motor retracts the lancing element from the skin in a second retraction phase of the retraction movement. This allows a favorable movement profile to be achieved by simple technical means. This is particularly important for test devices that are required to be produced in large numbers. The drive mechanism can be effectively designed for the rapid movement and the motor provided for the slow remaining movement can be designed to be compact and energy saving.

The drive motor advantageously supplies the drive mechanism with mechanical energy for automatic movement control.

Another improvement is achieved by means of the fact that the drive motor retracts the drive mechanism together with the lancing element as a combination in the second retraction phase.

A constructionally particularly advantageous embodiment provides that the drive mechanism has a cam control driven by means of a spring.

Another aspect of this disclosure concerns a method for withdrawing body fluid in which a forward and retraction movement of a lancing element is controlled by a lancing drive in such a manner that the lancing element is retracted in a first retraction phase of the retraction movement at a maximum retraction speed of more than 0.02 m/s and in which the lancing element is retracted from the skin during a second retraction phase for collecting body fluid in the receiving structure which follows the first retraction phase in such a manner that the collection period is in a range between 0.2 and 0.8 s and/or the retraction speed is between 0.8 and 1.5 mm/s.

BRIEF DESCRIPTION OF DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
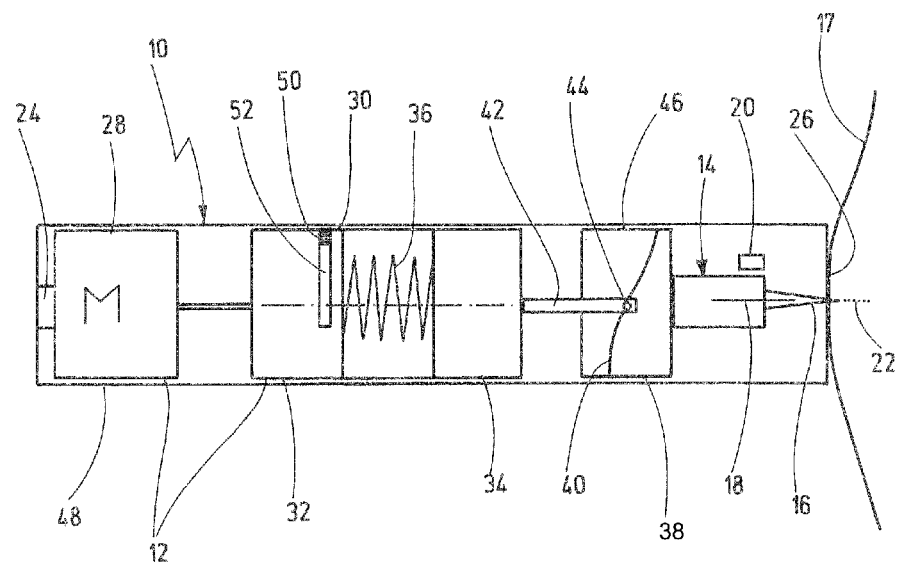
FIG. 1 shows a device for blood sugar tests with a multistage lancing drive in a simplified sectional diagram.

The device shown in FIG. 1 enables a user to himself remove a blood sample for analytical purposes and in particular for blood sugar monitoring. The device comprises a handheld device 10 with a lancing drive 12 for automatically handling a lancing element 14 used as a single-use article for blood withdrawal.

The lancing element 14 is designed as a so-called "microsampler" for collecting a small amount of blood from a body part 17 and in particular from a fingertip. As a monolithic one-piece molded part it can consist of thin stainless steel sheet and have a distally shaped tip 16 as a lancing member to produce a puncture wound. A groove-shaped or slot-shaped capillary channel 18 whose distal end section extends into the area of the tip 16, enables the uptake of body fluid (blood and/or tissue fluid) from the puncture wound. A test element 20 provided with a test chemistry which can be loaded with body fluid from the receiving structure 18 by making a suitable flow connection after the skin puncture can be used to detect the target substance (e.g., glucose) present in the body fluid. Blood glucose detection especially by means of contact-free optical methods is known in the prior art and is therefore not elucidated in more detail here.

The lancing drive 12 enables a controlled forward and retraction movement of the lancing element 14 along a lancing axis 22 where the lancing depth can be advantageously selected by the user in a range between 1 and 2.5 mm for adaptation to various skin types by means of an adjusting unit 24. The position of the skin surface can be optionally predetermined for the body part 17 by means of a positioning unit 26.

For a multiphase motion control the lancing drive 12 comprises an electrical drive motor 28 and a drive mechanism 30 that is pretensioned by the motor and operates purely mechanically. The drive mechanism 30 controls the rapid forward movement and a first rapid phase of the return movement whereas the drive motor 28 slowly retracts the lancing element 14 from the skin via the drive mechanism 30 in a second retraction phase. This allows the collection process to be optimized and made particularly user-friendly.

The mechanical drive mechanism 30 has a tensioning rotor 32 and a drive rotor 34 and the rotors are connected together by a pretensioned torsion spring 36. The drive mechanism 30 additionally comprises a cam drive or sliding gate drive 38 which translates the rotary motion of the drive rotor 34 into a translatory or lancing motion of the coupled lancing element 14 using a control cam 40. For this purpose the free end of a control arm 42 which extends from the drive rotor 34 engages in the circumferential control cam 40 by means of a cam slider 44. When the drive rotor 34 rotates, a stroke is generated corresponding to the cam slope whereby the cam drive 38 is guided by a linear guide 46 in the device housing 48. The relative rotation of the two rotors 32, 34 can be mutually limited by stop elements 50, 52 in order to take up the pretension of the spring 36 and to stop the drive rotor 34 in a desired rotation angle position. In a preparatory tensioning phase the drive rotor 34 is locked against rotation with respect to the housing 48 so that the spring 36 can be tensioned by the tensioning rotor 32 by rotating the motor 28 until the stop elements 50, 52 reach their initial position. The lock on the drive rotor 34 is released at a given angular position of the tensioning rotor 32 by a trigger that is not shown so that the drive rotor 34 instantaneously rotates in a spring-driven manner until the stop member 50 on the drive rotor side strikes against the other end of the stop groove 52 on the tensioning rotor side. In this manner it is possible to travel through an angular range of the control cam 40 in order to very rapidly execute the forward movement and the first retraction phase of the retraction movement.

Further details of a suitable drive mechanism are described in U.S. Publication No. 20100168618 which is incorporated herein by reference.

As mentioned, the drive side of the drive motor 28 is coupled to the tensioning rotor 32 in order to supply the mechanism 30 with mechanical energy in a preparatory tensioning phase. Another important function of the drive motor 28 is the controlled slow return movement of the lancing element 14 during the second retraction phase. In this process the stop elements 50, 52 are held in the end position described above by the remaining spring tension. As a result the drive mechanism 30 can be rotated further as a unit in order to travel through the remaining section of the control cam 40 during which the lancing element 14 is retracted at a defined retraction speed. In this phase the lancing member 16 which is still situated under the skin can take up sufficient blood from the partially vacated puncture wound by means of the collecting structure 18. The collected blood is subsequently transferred onto the test element 20 by a suitable actuation within preferably 0.5 s in a transfer step. For this purpose the test element 20 is arranged near enough to the receiving structure so that liquid transport takes place in the specified time taking into account the achievable transport rate.

Figure 2:
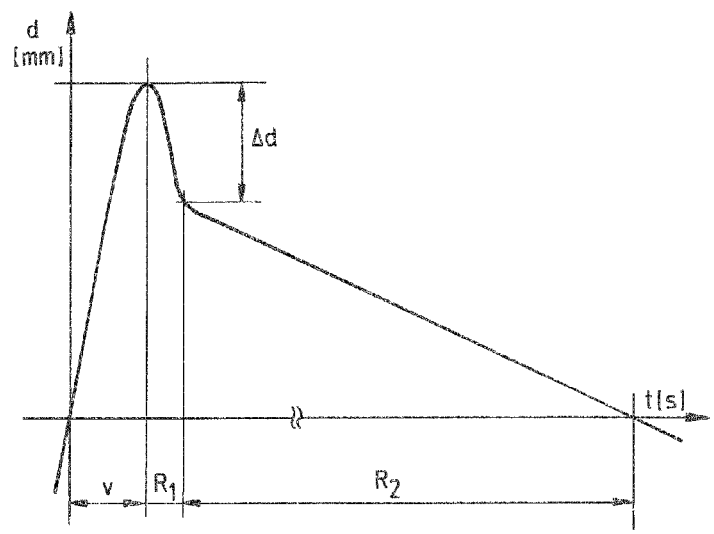
FIG. 2 shows a lancing profile when using the device according to FIG. 1.

The lancing profile shown in FIG. 2 is particularly advantageous for a blood collection that is as effective and pain-free as possible. In this connection the term "lancing profile" is to be understood as the time course of the lancing movement which is shown as a function of lancing depth over time.

In phase v of the forward movement, the tip 16 of the lancing element 14 strikes the skin at t=0 at a high speed and penetrates in one movement down to the desired puncture depth d. This depth must be individually optimized in order to extend through the epidermis to reach the dermis containing the blood capillaries. The duration of the forward movement is preferably between 0.3 and 0.7 ms.

Then in the first retraction phase R1 the tip 16 is pulled back by a predetermined distance Δd of about 0.5 mm to an intermediate position situated under the skin surface. This retraction position is preferably in the stratum corneum of the epidermis. This first retraction phase R1 should take place as rapidly as possible because the lancing element 14 which has been excited to vibrate by the sharp reversal of direction should not execute too many oscillation periods in the blood-carrying and innervated dermis. Hence, the maximum retraction speed reached shortly after the movement is reversed should be more than 0.02 m/s. Accordingly, the duration of the first retraction phase is limited to a range between 0.3 and 3 ms. As elucidated above, a uniform, harmonious sequence of motions is achieved in phases v and R1 by means of the drive mechanism 30.

The retraction of the lancing element 14 is considerably slowed at the end of the phase R1 so that the collection process can take place during the subsequent second retraction phase R2. In this connection, it has surprisingly turned out that the retraction speed should not fall below a minimum value and should still be high enough so that the skin tissue readily releases liquid. On the other hand, the collection period should be sufficiently long to allow the receiving structure or capillary 18 to collect the liquid which can take up to 500 ms taking into consideration production tolerances and aging effects. It must also be borne in mind than an excessive dwell period of the lancing element in the inserted state in the skin will be disagreeable to the user. In order to achieve a sufficient uptake of blood into the receiving structure 18, the speed of the lancing element in the second retraction phase should be substantially constant and a value between 1 and 1.5 mm/s is favorable. Such a relatively slow retraction can be achieved in an energy-saving manner by applying a voltage which is kept constant by simple means to a compact drive motor 28.

The lancing profile can be predefined independently of the lancing depth. In the case of a deeper puncture the curve shown in FIG. 2 is then, as it were, shifted upwards without alteration. Alternatively it may be of advantage to adapt the speed time course depending on a selectively changed lancing depth in such a manner that a defined dwell time is reached in the punctured state.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for withdrawing body fluid, comprising:
a lancing element adapted for puncturing the skin of a body part, the lancing element having a lancet tip and a receiving structure for collecting body fluid by capillary action;
a lancing drive for moving the lancing element in forward and return movements;
wherein, the duration of the return movement is longer than the duration of the forward movement, the return movement comprising a first retraction phase during which the lancing drive is configured to move the lancing element at a maximum retraction speed of more than 0.02 m/s, the first retraction phase followed by a second retraction phase for collecting body fluid into the receiving structure, the second retraction phase beginning with a retraction movement of the lancing element and continuing until the lancet tip exits the skin, the lancing drive being configured to move the lancing element during the second retraction phase for a duration of between 0.3 and 0.8 s and/or a retraction speed of between 0.6 and 2 mm/s.

2. The device of claim 1, wherein the lancing element is configured to retract during the first retraction phase a distance of up to 0.5 mm.

3. The device of claim 1, wherein the receiving structure is configured to be filled with body fluid during the second retraction phase while the lancing element still projects into the skin.

4. The device of claim 1, wherein the duration of the forward movement is between 0.3 and 0.7 ms.

5. The device of claim 1, wherein the duration of the first retraction phase is between 0.3 and 3 ms.

6. The device of claim 1, wherein the second retraction phase has a duration of between 0.4 and 0.5 s.

7. The device of claim 1, wherein the mean retraction speed of the lancing element during the second retraction phase is between 1.0 and 1.5 mm/s.

8. The device of claim 1, wherein maximum lancing depth is adjustable between 1 and 2.5 mm.

9. The device of claim 1, further comprising a variable lancing depth, wherein the speed of the lancing element during the return movement is adapted as a function of the variable lancing depth such that the lancing element is configured to remain inserted into the skin for a predetermined dwell period.

10. The device of claim 1, wherein the speed time course during the return movement of the lancing element is presettable independently of the lancing depth.

11. The device of claim 1, wherein the speed of the lancing element in the second retraction phase is essentially constant.

12. The device of claim 1, further comprising a test element for detecting an analyte and to which body fluid can be applied from the receiving structure.

13. The device of claim 12, wherein the total duration of the return movement of the lancing element is less than 2 s.

14. The device of claim 1, wherein the receiving structure comprises a channel configured to be brought into contact with the body fluid during skin puncture.

15. The device of claim 1, wherein the lancing drive has a drive motor and a mechanical drive mechanism, the drive mechanism controlling the forward movement and return movement.

16. The device of claim 15, wherein the drive motor supplies the drive mechanism with mechanical energy for automatic movement control.

17. The device of claim 15, wherein the drive motor is configured to retract the lancing element in the second retraction phase by means of the drive mechanism.

18. The device of claim 15, wherein the drive mechanism comprises a spring-driven cam control.

19. A device for withdrawing body fluid, comprising:
a lancing element adapted for puncturing the skin of a body part, the lancing element having a receiving structure for collecting body fluid by capillary action;
a lancing drive for moving the lancing element in forward and return movements;
a test element for detecting an analyte in the body fluid, the lancing drive configured to move the lancing element at a speed during the return movement such that the transfer time for transferring the body fluid from the receiving structure onto the test element is less than 0.5 s, wherein the total duration from the start of the return movement of the lancing element until completion of loading of the test element with the body fluid is less than 2 s;
further wherein the return movement comprises a first retraction phase followed by a second retraction phase, the second retraction phase configured for collecting body fluid into the receiving structure, the lancing drive being configured to move the lancing element during the second retraction phase at a retraction speed of between 0.6 and 2 mm/s, wherein the second retraction phase begins with a retraction movement of the lancing element and continues until the lancet tip exits the skin.

20. The device of claim 19, wherein the receiving structure comprises a channel configured to be brought into contact with the body fluid during skin puncture.

21. The device of claim 19, wherein the lancing drive has a drive motor and a mechanical drive mechanism, the drive mechanism configured to control the forward movement and retraction movement during a first retraction phase of the lancing element and the drive motor configured to effect the retraction movement of the lancing element in a second retraction phase.

22. The device of claim 21, wherein the drive motor is configured to supply the drive mechanism with mechanical energy for automatic movement control.

23. The device of claim 21, wherein the drive motor is configured to retract the lancing element in the second retraction phase by means of the drive mechanism.

24. The device of claim 21, wherein the drive mechanism comprises a spring-driven cam control.

25. A method of collecting body fluid with a lancing element having a tip and a receiving structure for collecting blood by capillary action, the method comprising:
inserting the tip of the lancing element into the skin of a body part to a puncture depth;
retracting the tip at a speed of more than 0.02 m/s during a first retraction phase; and then
retracting the tip during a second retraction phase during which body fluid is collected in the receiving structure, the second retraction phase beginning with a retraction movement of the tip and continuing until the tip exits the skin, the second retraction phase having a duration of between 0.3 and 0.8 s and/or the tip of the lancing element having a retraction speed of between 0.6 and 2 mm/s.

26. The method of claim 25, wherein the first retraction phase comprises retracting the tip of the lancing element a distance of up to 0.5 mm, the distance extending from the deepest puncture position into an intermediate position situated under the skin surface.

27. The method of claim 25, further comprising filling the receiving structure with body fluid during the second retraction phase.

28. The method of claim 25, wherein the step of inserting the lancet tip to a puncture depth has a duration of between 0.3 and 0.7 ms.

29. The method of claim 25, wherein the first retraction phase has a duration of between 0.3 and 3 ms.

30. The method of claim 25, wherein the second retraction phase has a duration of between 0.4 and 0.5 s.

31. The method of claim 25, wherein the lancet tip has an average speed of between 1 and 1.5 mm/s during the second retraction phase.

32. The method of claim 25, wherein the lancet tip has a substantially constant speed during the second retraction phase.

33. The method of claim 25, further comprising transferring the body fluid from the receiving structure onto a test element in less than 0.5 s.

34. The method of claim 33, wherein the total duration from the start of the retracting the tip at a speed of more than 0.02 m/s until completion of loading of the test element with body fluid is less than 2 s.

35. The device of claim 1, wherein the second retraction phase has a retraction speed of between 0.6 and 2 mm/s.

36. The device of claim 1, wherein the duration of the dwell time of the lancet tip during movement of the lancet tip in the second retraction phase is between 0.3 and 0.8 s.

37. The method of claim 25, wherein the second retraction phase has a retraction speed of between 0.6 and 2 mm/s.

38. The method of claim 25, wherein the duration of the second retraction phase extends until the lancet tip exits the skin.

39. The method of claim 25, wherein the duration of the dwell time of the lancet tip during movement of the lancet tip in the second retraction phase is between 0.3 and 0.8 s.

40. The device of claim 19, wherein the return movement comprises a first retraction phase followed by a second retraction phase, the second retraction phase configured for collecting body fluid into the receiving structure, the lancing drive being configured to move the lancing element during the second retraction phase at a retraction speed of between 0.6 and 2 mm/s.

41. A device for withdrawing body fluid, comprising:

a lancing element adapted for puncturing the skin of a body part, the lancing element having a receiving structure for collecting body fluid by capillary action; and a lancing drive for moving the lancing element in forward and return movements;

wherein, the duration of the return movement is longer than the duration of the forward movement, the return movement comprising a first retraction phase during which the lancing drive is configured to move the lancing element at a maximum retraction speed of more than 0.02 m/s, the first retraction phase followed by a second retraction phase for collecting body fluid into the receiving structure, wherein the duration of the dwell time of the lancet tip during the retraction movement in the second retraction phase is between 0.3 and 0.8 s and/or the average speed of the lancing element during the retraction movement in the second retraction phase is 0.6 to 2 mm/s.

42. The device of claim 41, wherein the receiving structure is configured to be filled with body fluid during the second retraction phase while the lancing element still projects into the skin.

43. The device of claim 41, wherein the duration of the forward movement is between 0.3 and 0.7 ms.

44. The device of claim 41, wherein the second retraction phase has a duration of between 0.4 and 0.5 s.

45. The device of claim 41, wherein the average retraction speed of the lancing element during the second retraction phase is between 1.0 and 1.5 mm/s.

46. The device of claim 41, further comprising a variable lancing depth, wherein the speed of the lancing element during the return movement is adapted as a function of the variable lancing depth such that the lancing element is configured to remain inserted into the skin for a predetermined dwell period.

47. The device of claim 41, wherein the speed time course during the return movement of the lancing element is presettable independently of the lancing depth.

48. The device of claim 41, wherein the speed of the lancing element in the second retraction phase is essentially constant.

* * * * *